United States Patent
Baumgartner

(10) Patent No.: US 9,084,431 B2
(45) Date of Patent: Jul. 21, 2015

(54) SPRAY-DRYING PROCESS FOR PRODUCING A DRY CARITINE POWDER OR GRANULATE

(75) Inventor: Max Baumgartner, Basel (CH)

(73) Assignee: LONZA LTD., Basel (CH)

( * ) Notice: Subject to any disclaimer, the term of this patent is extended or adjusted under 35 U.S.C. 154(b) by 867 days.

(21) Appl. No.: 11/988,095

(22) PCT Filed: Jul. 5, 2006

(86) PCT No.: PCT/EP2006/006551
§ 371 (c)(1),
(2), (4) Date: Dec. 31, 2007

(87) PCT Pub. No.: WO2007/003425
PCT Pub. Date: Jan. 11, 2007

(65) Prior Publication Data
US 2009/0082449 A1    Mar. 26, 2009

(30) Foreign Application Priority Data

Jul. 5, 2005   (EP) .................................. 05014529

(51) Int. Cl.
| | |
|---|---|
| A23K 1/00 | (2006.01) |
| A23K 1/16 | (2006.01) |
| A23L 1/305 | (2006.01) |
| A61K 9/16 | (2006.01) |
| A61K 31/205 | (2006.01) |
| A61K 31/221 | (2006.01) |
| C12P 13/00 | (2006.01) |

(52) U.S. Cl.
CPC ............... A23K 1/1609 (2013.01); A23K 1/002 (2013.01); A23L 1/305 (2013.01); A61K 9/1611 (2013.01); A61K 9/1664 (2013.01); A61K 31/205 (2013.01); A61K 31/221 (2013.01); C12P 13/007 (2013.01)

(58) Field of Classification Search
USPC .................................................... 424/54, 648
See application file for complete search history.

(56) References Cited

U.S. PATENT DOCUMENTS

| | | | | |
|---|---|---|---|---|
| 4,602,039 | A | * | 7/1986 | Cavazza ......................... 514/561 |
| 4,751,182 | A | * | 6/1988 | Sih ................. 435/128 |
| 5,071,874 | A | | 12/1991 | Scholl et al. |
| 5,073,376 | A | | 12/1991 | Kohl et al. |
| 5,124,357 | A | | 6/1992 | Newton et al. |
| 5,952,379 | A | * | 9/1999 | Fassi ............................ 514/561 |
| 6,472,011 | B1 | * | 10/2002 | Yakabe et al. ................ 426/583 |
| 2002/0198185 | A1 | | 12/2002 | Real et al. |
| 2003/0235646 | A1 | | 12/2003 | Nelssen et al. |
| 2005/0124558 | A1 | * | 6/2005 | Hassen .......................... 514/23 |

FOREIGN PATENT DOCUMENTS

| | | |
|---|---|---|
| EP | 0158194 A2 | 10/1985 |
| EP | 1020430 A1 | 7/2000 |
| EP | 1326502 B1 | 7/2003 |
| EP | 0722500 B1 | 1/2004 |
| WO | 92/18164 | 10/1992 |
| WO | 94/08627 | 4/1994 |
| WO | 02/061094 | 8/2002 |
| WO | 03/009854 A | 2/2003 |

OTHER PUBLICATIONS

Definition of Pre, The Free Dictionary, retrieved online on Jul. 30, 2013, http://www.thefreedictionary.com/pre-.*
The Free Dictionary, Slurry Definition, http://www.thefreedictionary.com/slurry, retrieved online on Jul. 28, 2014.*
Database WPI Week 199612, Derwent Publications Ltd., London, GB; AN 1996-112629.
Zimmermann et al., in Chirality in Industry II (Eds.: A. N. Collins, G. N. Shedrake, J. Crosby), John Wiley and Sons Ltd., Chichester, (1997), pp. 287 to 305.

* cited by examiner

*Primary Examiner* — Brian-Yong Kwon
*Assistant Examiner* — Jennifer A Berrios
(74) *Attorney, Agent, or Firm* — Hoffmann & Baron LLP

(57) ABSTRACT

A process for preparing a dry substantially pure and/or technical carnitine powder or granulate, from a substantially unpurified starting material containing a carnitine compound.

18 Claims, No Drawings

SPRAY-DRYING PROCESS FOR PRODUCING A DRY CARITINE POWDER OR GRANULATE

This application has priority benefit of International Application No. PCT/EP2006/006551, filed on Jul. 5, 2006, that has priority benefit of European Patent Application No. 05014529.1, filed on Jul. 5, 2005.

The present invention relates to novel processes for preparing a dry carnitine powder or granulate, which is substantially pure and/or has technical grade purity, in particular a dry L-carnitine powder or granulate, from a liquid starting material containing carnitine and the thus produced carnitine powder or granulate.

L-carnitine is a vitamin-like substance which is widely distributed in nature and has a broad range of pharmaceutical, food and feed applications. L-carnitine plays a central role in the metabolism of fatty acids by transporting them from the cytosol to the mitochondrial matrix for beta-oxidation. Long-chain fatty acid oxidation as energy source is carnitine-dependent in all tissues. By the administration of L-carnitine an insufficient L-carnitine production in the body can be compensated. The positive effects of L-carnitine are not only directed on energy metabolism, but also on the cardiovascular system, circulation, and muscular and nervous systems of the animal or human body. In addition, L-carnitine may be used for other purposes, including the stimulation of yeast and bacterial growth.

Increasing worldwide demand for L-carnitine has encouraged the search for ways of synthesizing it in an optically pure form. Its chemical synthesis produces a racemic mixture but the economics of the process is impaired by the costly selective precipitation necessary for L-isomer isolation. Also, the yields are low and to reduce costs it is necessary to recover and recycle the resolving agent. Although a certain part of the L-carnitine produced today involves these methods, there is a growing trend to obtain it by the biotransformation of cheap easily available substrates. One of the advantages of biotransformation in comparison to chemical synthesis is that the biotechnological processes are much more environmentally friendly. The amounts of waste water, total organic carbon, salts, and waste for incineration are all considerably lower for the biotransformation. Several processes for the biotechnological production of L-carnitine are known.

EP 0 158 194 B1 describes a process for the microbiological generation of L-carnitine on the basis of crotonobetaine and/or 4-butyrobetaine as starting compounds. In this process a microorganism which is able to produce L-carnitine from e.g. 4-butyrobetaine but cannot catabolize L-carnitine is cultivated with the starting compounds crotonobetaine and/or butyrobetaine in the presence of a growth substrate.

EP 0722 500 B1 describes a biotechnological process for the production of L-carnitine wherein the precursors crotonobetaine and/or γ-butyrobetaine are fermented in the presence of a suitable carbon and nitrogen source by means of a recombinant microorganism containing one or more of genes encoding those enzymes involved in the L-carnitine biosynthesis.

WO 02/061094 describes a microbiological method for producing L-carnitine on the basis of betaine esters as precursors wherein in a first step a betaine ester is converted into 4-butyrobetaine by an isolated hydrolase or a microorganism containing such a hydrolase and in a second step this betaine is converted into L-carnitine by a microorganism which is able to convert this betaine into L-carnitine.

In these whole-cell biocatalytic processes the L-carnitine produced is excreted into the culture medium, i.e. the fermentation broth from which it has to be isolated and purified. Thus, after fermentation the culture medium containing L-carnitine has to be subjected to several purification steps in order to obtain L-carnitine in a pure form which can be processed further. Usually the fermentation broth is subjected first to an ultrafiltration step to separate the biomass whereby a permeate containing L-carnitine is recovered. The obtained permeate is then subjected to a concentration step, an active carbon treatment for decolorisation, a desalination step and once again a concentration step whereby a concentrated very pure L-carnitine solution is obtained. This purified L-carnitine solution having a high purity is then subjected to a drying step.

Due to its high hygroscopicity the solid L-carnitine substance and also simple powder mixtures thereof have a poor storability and stability, in particular color stability, which causes serious problems such as inadequate flowability during the further processing of pure solid carnitine or powdered mixtures containing carnitine in the human food, animal feed or drugs industry. Thus, in order to reduce the hygroscopicity of the dry L-carnitine product the high-purity L-carnitine solution obtained after the last concentration step is frequently subjected to crystallization, re-crystallization and/or a spray drying process. Depending on what use is intended for the thus obtained dry L-carnitine product, further processing steps such as compactation etc. may follow.

Thus, in the conventional processes for the biotechnological production of L-carnitine always a very pure L-carnitine solution obtained by applying a multitude of different purification methods to the fermentation broth is subjected to crystallization or re-crystallization and/or a spray-drying step in order to obtain a dry less hygroscopic or non-hygroscopic L-carnitine product which thereafter can be stored or further processed according to the intended use. However, so far these conventional processes do not provide for a direct capture of the L-carnitine from an unpurified culture medium obtained after fermentation or a from a pre-purified culture medium subjected only to a preliminary purification, e.g. by applying only one or a few purification steps. These various separation and purification steps that are conducted in the conventional downstream processing of fermentation broth containing L-carnitine render the entire biotechnological production process not only laborious and time-consuming but also cost-intensive due to the different technical equipment necessary for conducting the diverse purification steps. Thus, both from an operational and economic view the conventional downstream processing of the fermentation broth has several disadvantages.

Therefore, the technical problem underlying the present invention is to provide a process for a simple and efficient purification of carnitine from an unpurified or pre-purified starting material containing carnitine, in particular a starting material which contains in addition to carnitine still a plurality of different lower-molecular accompanying substances, which on the one hand allows to improve the overall efficiency and speed of the purification of carnitine from that starting material and to reduce significantly the costs and on the other hand ensures a high yield and high purity of carnitine isolated.

The present invention solves this technical problem by providing a first process for preparing a dry carnitine powder or granulate from a liquid starting material containing carnitine, comprising the steps of a) mixing the starting material with a carrier b) subjecting the mixture obtained in a) to a drying process and c) recovering a stable dry carnitine powder or granulate.

The present invention also solves this technical problem by providing a second process for preparing a dry carnitine powder or granulate from a liquid starting material containing carnitine comprising the steps of
 a) subjecting the starting material to a drying process to obtain a dried product
 b) mixing the dried product obtained in a) with a carrier and
 c) recovering a stable dry carnitine powder or granulate.

Surprisingly and unexpectedly the inventors of the present invention have found that, if a pre-purified or substantially unpurified fermentation broth derived from a biotechnological process for the production of L-carnitine, in particular a L-carnitine containing permeate obtained by ultrafiltrating this fermentation broth, is subjected to a spray-drying process, a stable dry L-carnitine product can be obtained that has characteristics which are highly comparable to that of a dry L-carnitine product obtained by conventional methods, i.e. spray-drying of a very pure L-carnitine solution.

It is known, that the starting material used by the inventors in these experiments, i.e. the permeate obtained by ultrafiltration a fermentation broth, is still a rather complex medium containing a plurality of diverse accompanying substances. By a preliminary purification step such as ultrafiltration, e.g. by using a membrane with a cut-off of 50 000 kDA, only accompanying substances with a given size, in particular suspended solids and solutes of a molecular weight greater than 50 000 kDa such as floating particles, colloids, macromolecules, cells and cell debris are removed, whereas accompanying substances such as organic compounds with a lower molecular weight, waste products and salts, which represent the majority of all accompanying substances will be obtained in the permeate. In view of this rather unpurified starting material used for the spray-drying process which still contains a plurality of different accompanying substances it is therefore surprising that the inventors could show that a substantially pure and/or technical dry L-carnitine product can be obtained therefrom, if the permeate is either first mixed with an appropriate particulate carrier material and then subjected to a drying process, in particular a spray-drying process or alternatively, is first subjected to a drying process, in particular a spray-drying process and then immediately mixed with such a particulate carrier material. This shows that in contrast to the conventional approaches it is possible to omit most of the purification steps traditionally conducted in downstream processing in the biotechnological carnitine production.

The stable dry powdery carnitine products obtained by the inventive processes mainly consist of the carnitine compound and the carrier material admixed whereas all other components originally present in the starting material such as lower-molecular organic substances are only present in low quantities. In comparison to powders obtained by spray-drying of a very pure carnitine solution purified in conventional way the carnitine products obtained by the inventive processes do not comprise substantially higher amounts of accompanying substances. Thus, the carnitine products obtained by the inventive processes are substantially pure. Furthermore, the carnitine products obtained according to the invention show in comparison to carnitine products obtained by spray-drying of pure carnitine solutions a similar low hygroscopicity, a similar high flowability, a similar excellent storability and a comparable workability. Due to their remarkable and advantageous properties the dry carnitine products obtained by the inventive processes therefore can be processed in a similar way as carnitine powders obtained by spray-drying of pure carnitine solutions. The dry carnitine products obtained by the inventive processes have advantageously low water content and are particularly suited for the production of animal feed, but can also be used for the production of foodstuff, pharmaceutical compositions and cosmetic compositions.

In comparison to conventional purification methods thus, the inventive processes exhibit great advantages of both an operational and economic nature. Due to the fact that according to the inventive processes before spray-drying not more than one purification or separation step has to be conducted, but not five or more steps as in the conventional processes, the inventive processes allow a rapid generation of spray-dried pure carnitine powders or granulates. Accordingly all that equipment usually needed for conducting these purification steps can be omitted. Therefore, and also since according to the invention for the spray-drying step the already available conventional spray-drying devices can be used the processes of the present invention provide for significant cost benefits.

Thus, the invention provides particularly simple, efficient and economic processes for providing substantially pure and/or technical dried carnitine powders exhibiting excellent flowability, stability and storability and also low hygroscopicity.

In the context of the present invention "carnitine" or "carnitine compound" includes for example L-carnitine, an alkanoyl-L-carnitine, a derivative thereof, a salt thereof or a mixture thereof, without being restricted thereto. The alkanoyl-L-carnitine is a carnitine compound having an alkanoyl group whereby the alkanoyl group is preferably a straight or branched group, having from 2 to 8 carbon atoms, more preferred from 2 to 6 carbon atoms. Particularly preferred the alkanoyl-L-carnitine is acetyl-, propionyl-, butyryl-, valeryl- or isovaleryl-L-carnitine.

The salt of the carnitine compound can include for example the aspartate, citrate, phosphate, fumarate, lactate, maleate, oxalate, hydroxycitrate or tartrate salts of L-carnitine and alkanoyl-L-carnitine.

According to the invention the liquid starting material can be a substantially unpurified liquid starting material, a purified liquid starting material or a mixture thereof. In the context of the invention a "substantially unpurified liquid starting material" is a pre-purified liquid feedstock containing a carnitine compound that can be used for a drying step, in particular a spray-drying step, in order to obtain a substantially pure powdery or granular carnitine product exhibiting low hygroscopicity and ready for use in food and feed applications, in particular animal feed applications. The pre-purified liquid starting material is derived from an unpurified liquid starting material that has been subjected to a preliminary purification whereby only a few purification and/or separation steps have been conducted. In the context of the present invention a "purification step" is a method which is suitable for obtaining a given chemical substance of a certain purity grade. Examples for purification methods include, without being restricted to, filtrations such as ultrafiltration, active carbon decolorization, centrifugations, crystallization, precipitations etc. A "preliminary purification" includes preferably a single purification and/or separation step such as whole filtration methods, e.g. ultrafiltration, or centrifugation, in order to remove a certain part of those accompanying substances originally present in the untreated starting material. In the context of the present invention the expression "removing a part of accompanying substances" can mean that due to the preliminary purification particular accompanying substances or macromolecules are completely or almost completely removed from the starting material whereas other accompanying substances will completely or almost completely remain in the pre-purified starting material. For example it is possible that by the preliminary purification accompanying substances falling into a particular group of compounds with a common feature such as a certain size are completely or almost completely removed from the starting material whereas other accompanying substances falling in another size group remain completely or almost completely in the pre-purified starting material. However, "removing a part of the accompanying substances" can also mean that the amount of all or nearly all different accompanying substances is partially reduced. According to the invention the preliminary purification removes about 20%-90% of the accompanying substances originally present in the unpurified starting material, preferably about 40%-90% of the accompanying substances and more preferred about 60%-90% of the accompanying substances. Most preferred the preliminary purification removes about 80%-90% of all accompanying substances originally present.

Thus, in the context of the present invention the pre-purified liquid starting material contains apart from the carnitine compound and a fluid or solvent, in particular water, at least one group of additional contaminants or accompanying substances, e.g. one or more salts, one or more waste products of the fermentation process, not converted precursor molecules of the carnitine compound etc. Usually the pre-purified starting material contains a plurality of different accompanying substances. The unpurified liquid starting material used according to the present invention typically contains from 5 to approx. 70% by weight of dry substance. Thus, depending on the content of dry substance the substantially unpurified liquid starting material can have the form of a solution, suspension or paste. In the pre-purified starting material the proportion of the carnitine compound in the total dry substance is in the range of 50%-90%, more preferred in the range of 60%-90% and most preferred approx. 80-90%. The proportion of all accompanying substances or contaminants in the total dry matter is in the range of 10% to less than 50%, preferably 10% to less than 40% and more preferred approx. 10%-20%.

In a preferred embodiment of the invention the substantially unpurified liquid starting material is a permeate derived from an ultrafiltration of a fermentation broth obtained in a biotechnological carnitine production process. This fermentation broth can be for example derived from a whole-cell biocatalytic process such as a culture medium in which microorganisms were cultivated in order to convert an appropriate reactant such as 4-butyrobetaine into the carnitine compound.

In the context of the present invention "ultrafiltration" is a selective separation technique for solutions containing macromolecular substances. Ultrafiltration is a membrane separation techniques which is operated by applying a hydrostatic pressure. Usually pressures up to 145 psi (10 bar) are applied. The membranes used include flat membranes, spiral membranes, tubular/straw membranes and ceramic membranes. By ultrafiltration suspended solids and solutes of a molecular weight greater than 1,000 kDA, preferably greater than 50 000 kDa such as floating particles, colloids, macromolecules, bacteria or viruses can be separated. The ultrafiltrate or permeate obtained contains low-molecular weight organic solutes and salts.

In another preferred embodiment of the invention the substantially unpurified starting material is a liquid reaction mixture derived from a large scale chemical synthesis of the carnitine compound which was subjected to a preliminary purification, e.g. a chromatographic step. For example the known techniques of large scale synthesis of L-carnitine include inter alia the optical resolution of a racemic mixture, whereby a resolving agent is used and the unwanted enantiomer is separated, the stereospecific hydration of crotonobetaine or γ-butyrobetaine, the enantioselective reduction of a butyric 4-chloro-3-oxoester by means of mono- or bimetallic ruthenium catalysts, which results in the formation of the corresponding 3-hydroxy derivative which by reaction with trimethylamine and hydrolysis of the ester group, is converted to L-carnitine or the enantioselective reduction of an alkyl 4 chloro-3-oxobutyrate or 4-chloro-3-oxobutyramide.

In the context of the present invention a "purified liquid starting material" is a liquid feedstock which was derived from an unpurified liquid starting material that has been subjected to several purification and/or separation steps whereby the accompanying substances or contaminants were completely or almost completely removed. According to the invention by these purification and/or separation steps more than about 90% of the accompanying substances originally present in the unpurified starting material, preferably more than about 95% of the accompanying substances and more preferred more than about 97% of the accompanying substances have been removed.

A particular preferred embodiment of the invention relates to a process for preparing a dry L-carnitine powder or granulate from a substantially unpurified liquid starting material containing L-carnitine, comprising the steps of a) mixing the starting material with a carrier, b) subjecting the mixture obtained in to a drying process and c) recovering a stable dry L-carnitine powder or granulate.

Another preferred embodiment of the invention relates to a process for preparing a dry L-carnitine powder or granulate from a substantially unpurified liquid starting material containing L-carnitine, comprising the steps of a) subjecting the starting material to a drying process to obtain a dried product, b) mixing the dried product obtained in a) with a carrier and c) recovering a stable dry L-carnitine powder or granulate.

In the context of the present invention a "carrier" or "carrier material" is a chemically inert substance which preferably consists of discrete particles. Preferably, the carrier consists of microparticles of a defined size range. Suitable carrier materials include on one hand inorganic materials, for example salts or materials based on silica, and on the other hands organic compounds, such as sugars. The selection of the carrier depends on the intended use of the dry L-carnitine powder recovered at the end of the inventive process.

If the carnitine powder or granulate, e.g. the L-carnitine powder or granulate, for example shall be processed to a finished product for a therapeutic or prophylactic use, in particular to treat and/or prevent an animal disease it is preferred that the carrier to be used is selected from the group consisting of a galenic auxiliary agents. Examples of galenic auxiliary agents include, without being restricted to, compounds such as lactose, maltodextrin, dextrin, dry glucose, starch, microcrystalline cellulose, chemically and/or physically modified microcrystalline cellulose or derivatives thereof, blends of microcrystalline cellulose and silicon dioxide, polyethylene glycol, magnesium stearate, precipitated silicic acid, precipitated silica, dispersed silica, sorbitol, mannitol or mixtures thereof.

If the carnitine powder or granulate, e.g. the L-carnitine powder or granulate, is used for the production of animal feed it is preferred that wheat pollard, precipitated silica, silica particles, floury or granulated diatomaceous earth, calcium carbonate and/or mixtures thereof are used as carriers.

Wheat pollard is a by-product of the wheat milling industry. It is known that wheat pollard is an excellent binding material for pelletised feed. Due to its content of crude protein, crude fat and crude fiber wheat pollard has an energy level which is approximately equal to that of oat.

Precipitated silica is sold commercially for example by Bayer AG under the trademark "Silcasil". These products are amorphous synthetic silicas produced by precipitation of waterglass with acids. Special types of Silcasil with a mean particle size of more than 100 μm can be used as carriers for powdery feedstuffs as well as flow-promoting agents which furthermore have anti-caking effects. Other amorphous precipitated silica include Tixosil commercially sold by Rhodia Silicas Silica particles with a wide size range and different shapes are sold commercially for example by Degussa under the trademark "Sipernat". For example Sipernat 50 is a silica with mainly spherical particles with a particle size of approx. 7.5 μm. Sipernat 22 has an average particle size of 7.0 7.5 μm. Sipernat 2200 is a microgranular silica with a particle size of approx. 320 μm.

Floury and granulated diatomaceous earth is commercially sold under the trademark "Diamol". More than 90% of the particles in floury Diamols have a size between 5 and 63 microns whereas particles of granulated Diamol have a size in the mm range.

Calcium carbonate, e.g. calcite, is preferably used in milled form.

According to the first process of the invention for preparing a dry carnitine powder or granulate the purified or substantially unpurified liquid starting material containing carnitine is first mixed with the carrier or a mixture of different carriers and then subjected to a drying process. In contrast, according to the second process of the invention for preparing a dry carnitine powder or granulate the purified or pre-purified starting material is first subjected to a drying process and then mixed with the carrier. In the latter process it is preferred that after drying the starting material the dried product obtained is immediately mixed with the carrier whereby the dried product should be sieved in order to remove any lumps.

In the context of the invention "a drying process" is a process by which a chemically unbound fluid, e.g. water or an inorganic or organic solvent, is removed from a liquid, gaseous or solid material by heating or by addition of a moisture binding agent. In the thermal drying moisture is removed by evaporation.

In a preferred embodiment of the invention the drying process used for drying the mixture of carnitine and carrier material involves the conduction of a spray-drying process. According to the invention spray-drying is preferably used for drying liquid starting materials such as solutions or suspensions. Such liquid starting materials may have a dry substance content of about 40% to 80% or less. Preferably the dry substance content is less than 40%, less than 30% or less than 20%, based on weight. Particularly preferred a liquid starting material to be subjected to spray-drying has a dry substance content of less than 10% based on weight.

In the context of the present invention "spray-drying" is a process for dehydrating or drying a fluid containing one or more compounds which shall be recovered in form of a dry powdery and/or granulated product. Spray-drying is highly suited for the continuous production of dry solids in either powder, granulate or agglomerate form from a liquid feedstock such as a solution, emulsion and pumpable suspension. Preferably, the product of a spray-drying process is a free flowing particulate product with well-defined characteristics regarding particle size distribution, residual moisture content, bulk density, and particle shape.

Spray-drying consists of at least four separate process stages, namely a) atomization of a liquid feedstock into a spray of droplets, b) contacting the droplets with hot air in a drying chamber, c) drying, i.e. evaporation of moisture from the droplets and formation of dried particles, and d) separation of the dried product from the drying air. Atomization involves the formation of droplets with a desired droplet size distribution. Atomization is generally accomplished by the use of a single-fluid nozzle, a two-fluid-nozzle or a rotary atomizer. After formation of the droplets these are brought into contact with drying air within a dryer. Design and operating condition of the dryer are selected according to the drying characteristics of the product and powder specification. The contact between droplets and drying air in the dryer can occur in a co-current mode, a counter-current mode or a mixed-flow mode. The evaporation of moisture from the droplets and formation of dry particles proceed under controlled temperature and airflow conditions. The drying step occurs in two phases. The first phase is the constant-rate step, in which moisture rapidly evaporates from the surface, and capillary action draws moisture from within the particle. In the second phase, diffusion of water from to the surface controls the drying rate. As moisture content drops, diffusion rate also decreases. Removing the last few percent of moisture in a single-stage dryer is responsible for most of the residence time in the dryer.

According to the invention atomization of the liquid starting material, i.e. the formation of a spray having a desired droplet size distribution can be accomplished by a single-fluid (or pressure) nozzle, a two-fluid nozzle, or a rotary atomizer which is also known as spinning disc or a wheel. The single-fluid nozzle allows more versatility in terms of positioning with the spray chamber, so the spray angle and spray direction can be varied. Since particle size is at least partially dependent on the feed rate, nozzles have more limitations in terms of product characteristics and operating rates. Once the nozzle is in place, rate can only be varied by pressure. In high-volume operations, frequently several nozzles are located within the chamber and positioned so constant evaporation conditions are maintained around each nozzle. For more viscous feeds, two-fluid nozzles can be utilized, with air being the second medium to move the feed and effectively atomize it. Air can be mixed internally within the nozzle or externally to the nozzle. The liquid feed also can be dispersed and atomized by centrifugal force on a rotary or spinning disc. In this case particle size is primarily controlled by the wheel speed. By using a rotary disc the liquid feed is distributed to the centre of the disc, travels over the surface as a thin film and is flung from the edge as small droplets. In general nozzles and wheels are capable of producing virtually identical particle types. The particle appearance can further be varied by additional measures. For example steam injection eliminates air in the droplet, resulting in a highly dense, higher bulk-density powder.

According to the invention the contact between the droplets formed by atomization with hot air in a drying-chamber can be accomplished by a co-current mode, a counter-current mode or by a mixed flow mode. The co-current mode is characterized in that drying air and particles move through the chamber in the same direction. In the counter-current movement drying air and particles move in opposite directions. When this mode is applied then the temperature of the powder leaving the dryer is higher than the exhaust air temperatures. In the mixed-flow mode particle movement experiences both co-current and counter-current phases. This mode is suitable for products comprising a more coarse powder. The mixed-flow mode can be conducted by using nozzle atomizers, which spray droplets upwards into an incoming airflow or spray droplets downwards towards an integrated fluid bed.

According to the invention in the final phase of spray-drying the dried carnitine product is removed from the air in a pollutant-free manner, wherein preferably the fines are collected separately, e.g. with cyclones, bag filters, electrostatic precipitators or scrubbers. The thus collected fines are preferably returned to another agglomeration process.

As disclosed in more detail in WO 92/18164 and WO 94/08627 the conditions of spray-drying can be controlled so that microparticles having a defined size range, e.g. 0.1 to 50 µm, or microgranules with a size of 5 to 500 µm can be obtained. Precise conditions for spray-drying vary in accordance with the liquid starting material used, e.g. with the type of the fluid, and the carrier material employed. If the fluid is water, than according to the invention the fed-in drying air has usually a temperature in the range of 120-350° C. Particularly preferred the temperature of the fed-in drying air is approx. 210-270° C. Most preferred spray-drying is conducted at a temperature of the fed-in drying air in the range of 230-250° C. According to the invention the temperature of the air at the outlet is preferably in the range of 100-140° C., particularly preferred in the range of 115-125° C.

In another preferred embodiment of the invention the drying process used for drying the mixture of the carnitine compound and carrier material is carried out in a whirl drier. According to the invention drying in a whirl-drier is preferable used for drying liquid starting materials having a dry substance content of more than 40% based on weight, in particular more than 50% up to approx. 70%.

According to a further embodiment of the inventive process it is possible to add one or more additional compounds to the starting material and/or to the carrier before drying and/or to the dry carnitine powder or granulate obtained after drying. This way it is possible to obtain combination products which for example contain apart from the carnitine compound additional active ingredients.

These additional compounds can be substances that are suitable as food ingredients or food additives. In the context of the present invention the term "food ingredient" means a single substance or a mixture of substances which optionally can contain one or more additives and which serve for nutrition of human beings and can be consumed by human beings in an unprocessed, processed and/or formulated state. A "food additive" is a substance that is added to a foodstuff to alter certain features of this foodstuff such as appearance, constitution, consistency, taste, odor, storability, workability etc. or for physiological or nutritional reasons. Examples for food additives include, without being restricted to, sweeteners, bulking agents, flavoring agents, acidifying agents, preservative agents, mineral matter, vitamins, amino acids, antioxidants, enzymes, pigments, emulsifying agents, agents that improve compaction and the like.

These additional compounds can also be substances that are suitable as feed ingredients or feed additives. In the context of the present invention the term "feed ingredient" means a single substance or a mixture of substances which optionally can contain one or more additives and which is destined to be fed in unprocessed, processed and/or formulated state to animals such as poultry, pigs, cattle, horses, fishes and pets. A "feed additive" is a substance that is added to a feed to alter certain features of the feed such as appearance, constitution, consistency, taste, odor, storability, workability etc. or for physiological or nutritional reasons. Examples for feed additives include, without being restricted to, minerals, vitamins, amino acids, urea, bulking agents, preservative agents, flavoring agents, acidifying agents, agents for improving growth or utilization of feed ingredients, antioxidants, enzymes, pigments, emulsifying agents, agents that improve compaction and the like.

The additional compounds can also be substances or substance mixtures that are conventionally used for the preparation of a pharmaceutical composition, without being themselves active ingredients or agents. A "pharmaceutical composition" is a substance or formulation which upon application to or within an animal or human body can cure or heal and/or relieve and/or prevent a certain condition, disease, suffering or injury or which can restore certain functions of a tissue or organ of that body to the normal. Substances which are commonly used for the preparation of pharmaceutical compositions and which are not themselves active agents include, without being restricted to, excipients, lubricants, flavoring agents, disintegrants, binding agents and the like.

It is also possible that the additional compounds are substances conventionally used for the preparation of a cosmetic composition.

It is also possible that the additional substances are active agents which have in comparison to the carnitine compound a similar or different biological activity.

By the addition of the one or more additional compounds it is possible to obtain a combination product that, depending on the particular compound(s) added, can be used either directly as foodstuff, feedstuff, cosmetic preparation and pharmaceutical composition, respectively, or for the preparation thereof.

According to the invention it is possible to add this additional compound(s) to the starting material before the starting material is mixed with the carrier or before the starting material is dried. However, it is also possible to add this additional compound to the carrier before the carrier is added to the liquid or to the already dried starting material. According to the invention it is, however, also possible to add this additional compound to the dry carnitine powder comprising carnitine and carrier.

In a preferred embodiment the additional compound is an amino acid, in particular lysine. From U.S. Pat. No. 5,124,357, the entire disclosure of which is incorporated by reference into the present application, it is known that feeding a diet supplemented with L-carnitine and lysine to finishing pigs increases weight gain and feed utilization.

In another preferred embodiment the additional substance is a chromium compound.

Chromium is a trace mineral that is involved actively in the metabolism of carbohydrates, lipids, proteins, and nucleic acid. Chromium potentiates insulin action by increasing the cellular uptake of glucose and intracellular carbohydrate and lipid metabolism. From US 2002/0198185 A1, the entire disclosure of which is incorporated by reference into the present application, it is known that feeding of a diet supplemented with L-carnitine plus a trivalent chromium salt such as chromium (III) picolinate or chromium nicotinate to a sow during gestation, lactation, breeding and/or prebreeding enhances the reproductive performance.

In a further preferred embodiment the additional substance added is a vitamin such as niacin or niacinamide, vitamin C, vitamin A, vitamin E and the like. The additional substance can also be coenzyme Q10.

In another preferred embodiment the additional substance is alpha-lipoic acid. Alpha-lipoic acid is a coenzyme for the pyruvate dehydrogenase complex in the mitochondrial matrix. It is an essential cofactor for metabolism in alpha-ketoacid dehydrogenase reactions. This vitamin-like substance has been supplemented orally for health benefits and has also been used as a therapeutic agent in a variety of hepatic and neurological disorders.

In another embodiment of the present invention the additional compound is ractopamine that belongs to the class of compounds that bind beta-adrenergic receptors and promote the accretion of muscle protein while reducing body fat. From US 2003/0235646 A1, the entire disclosure of which is incorporated by reference into the present application, it is known that feeding of a diet supplemented with L-carnitine plus ractopamine to finishing pigs results in an improvement of the quality of meat.

Another aspect of the present invention relates to a process for preparing a dry carnitine powder or granulate from an unpurified liquid starting material containing a carnitine compound, comprising the steps of
 a) subjecting the starting material to a preliminary purification, in particular to one purification step
 b) mixing the thus pre-purified starting material with a carrier
 c) subjecting the mixture obtained in b) to a drying process and
 d) recovering a stable dry carnitine powder or granulate with a low water content.

A further aspect of the present invention relates to a process for preparing a dry carnitine powder or granulate from an unpurified liquid starting material containing a carnitine compound comprising the steps of
 a) subjecting the starting material to a preliminary purification, in particular to one purification step
 b) subjecting the pre-purified starting material to a drying process to obtain a dried product
 c) mixing the dried product obtained in b) with a carrier and
 d) recovering a stable dry carnitine powder or granulate with a low water content.

The technical problem underlying the present invention is also solved by providing a process for preparing a dry L-carnitine powder or granulate, which is particularly suitable for the production of a feed product comprising the steps of
 a) conducting a biocatalytic process for the production of L-carnitine in a liquid medium,
 b) subjecting the medium to pre-purification step to obtain an pre-purified liquid containing L-carnitine
 c) subjecting the pre-purified liquid to a drying process in order to obtain a dried product and mixing the dried the dried product with a carrier, or alternatively, mixing the pre-purified liquid with a carrier and subjecting the mixture obtained to a drying process, and
 d) obtaining a dry powder of L-carnitine.

Thus, the first step of the inventive process comprises a biocatalytic process for the production of L-carnitine. According to the present invention a "biocatalytic process" or a "biotransformation" is an enzyme-catalyzed conversion of a non-natural substrate, i.e. precursor, to the product desired. In the context of the invention a biocatalytic process may also include one or more chemical synthesis steps, for example a synthesis step for obtaining an intermediate product which then is converted by biological means into the product desired or a further intermediate product. The enzymes needed in the biocatalytic process may be used in a number of forms. They may be wild-type, or recombinant, or genetically modified to increase their specificity or activity. One or more or all of the enzymes needed in the biocatalytic process may also be present in whole cells, in particular microbial or mammalian cells which may be living or dead cells. Living cells include for example growing, resting or immobilized cells. Alternatively, cell-free enzymes, in particular isolated and/or purified enzymes may be used. The enzymes employed can be used in solution, in a membrane reactor, as a suspension, in a cross-linked form or as immobilized enzymes. The medium for the enzymatic reaction may be aqueous, organic or two-phase.

Thus, according to the invention the biocatalytic process can be a process in which either cells, preferably microbial cells, or isolated enzymes are used to convert a precursor compound such as 4-butyrobetaine into L-carnitine. However, the biocatalytic process may also involve the combined use of whole cells and isolated enzymes.

In a preferred embodiment the biocatalytic process for the production of L-carnitine involves the use of at least one microorganism capable of producing L-carnitine from a suitable precursor compound. This microorganism is cultured in a suitable medium containing a precursor of L-carnitine such as a fermentation medium containing e.g. 4-butyrobetaine and/or crotonobetaine under conditions allowing the biotransformation of this precursor to L-carnitine and its excretion into the medium.

Preferably in the biocatalytic process microorganisms are used that contain one or more or all of the genes encoding 4-butyrobetainyl-CoA synthetase, 4-butyrobetainyl-CoA dehydrogenase, crotonobetainyl-CoA hydrolase and thioesterase which form a naturally occurring pathway for converting 4-butyrobetaine into L-carnitine. The enzyme 4-butyrobetainyl-CoA synthetase can convert 4-butyrobetaine into 4-butyrobetainyl-CoA which then can be converted by 4-butyrobetainyl-CoA dehydrogenase into crotonobetainyl-CoA. Crotonobetainyl-CoA is converted by crotonobetainyl-CoA hydrolase into L-carnityl-CoA which is then converted by thioesterase into L-carnitine. The biotransformation process for the production of L-carnitine by the use of such microorganisms has a high energy requirement due to the necessity of cofactor regeneration and the transport of the precursor 4-butyrobetaine added to the medium across the cell membrane into the cell and the transport of the L-carnitine produced from the cell across the cell membrane into the medium. For this reason the biocatalytic process should be carried out with growing cells or cells that are in a maintenance state, which has the advantage of low biomass production and high metabolic activity.

The microbial cells used can naturally contain one or more or all of the genes encoding 4-butyrobetainyl-CoA synthetase, 4-butyrobetainyl-CoA dehydrogenase, crotonobetainyl-CoA hydrolase and thioesterase. Alternatively, the microbial cells used can be recombinant cells in which one or more or all of these genes have been introduced by DNA recombination techniques. Preferably the microorganism used in the biocatalytic process for the production of L-carnitine is not capable to catabolize L-carnitine or its capability to catabolize L-carnitine is completely or partially inhibited. Thus, in order to prevent degradation of L-carnitine the microbial cells used in the biocatalytic process do not contain a gene encoding carnitine dehydrogenase or carry a mutation in this gene.

Particularly preferred the microorganism used for the biocatalytic process is the one described by Zimmermann et al., in: Chirality in Industry II (Eds.: A. N. Collins, G. N. Sheldrake, J. Crosby), John Wiley and Sons Ltd, Chichester (1997), pp. 287-305, the entire disclosure of which is incorporated by reference into the present application. This microorganism belongs to a genus related to *Agrobacterium* and *Rhizobium*.

Of course also those microorganisms can be used in the biocatalytic process that are described in EP 0722 500 B1, the entire disclosure of which is incorporated by reference into the present application. In this embodiment recombinant microorganisms are used that can contain one or more of the genes bocC, boc A/B and bocD of the L-carnitine biosynthetic pathway. These microorganisms can belong to the genera *Escherichia, Pseudomonas, Agrobacterium, Rhizobium*, and *Comamonas*. These microorganisms can convert the precursor compounds crotonobetaine and/or 4-butyrobetaine into L-carnitine.

Further microorganism to be used in the biocatalytic production of L-carnitine include those described in WO 02/061094, the entire disclosure of which is incorporated by reference into the present application. These microorganisms contain a hydrolase which can convert a betaine ester such as 4-butyrobetaine methyl ester into 4-butyrobetaine.

According to the invention thus preferred examples of the precursor of L-carnitine to be used in a biocatalytic process include, without being restricted to, crotonbetaine, 4-butyrobetaine and betaine esters such as 4-butyrobetaine methyl ester.

The composition of suitable media used for the cultivation of microbial cells and conditions of culturing the microbial cells in order to effect the biotransformation of the precursor compounds to L-carnitine are known in the art. Suitable media and culture conditions are for example described in WO 02/061094, EP 0722 500 B1 and EP 0 158 194 B1 the disclosure of which concerning media composition and culture conditions is incorporated by reference into the present application.

Another aspect of the present invention relates to a dry carnitine powder or granulate obtainable by any one of the inventive processes.

The carnitine powder obtained by any one of the processes of the present invention consists of a homogenous mixture of discrete particles, in particular microparticles. Usually these particles have a size in the range of about 0.1 to 50 μm. The carnitine granulate consists of a homogenous mixture of granules, in particular microgranules. Granules are in fact agglomerated particles. Usually the granules have a size in the range of about 5 to 500 μm.

The inventive dry carnitine powder or granulate is "substantially pure" in that it consists of carnitine and amounts of those carrier materials used in the drying process whereas contaminants or accompanying substances originally present in the liquid starting material are only present in minor amounts. The amount of accompanying substances in the dry carnitine powder obtained depends on the purity of the liquid starting material. If for example the starting material used was a L-carnitine containing permeate, i.e. a substantially unpurified starting material, then the accompanying substances are present in an amount of not more than 10% relative to the L-carnitine content. Thus the purity of the inventive carnitine powder or granulate is of at least technical grade. However, if a purified liquid starting material was used then the inventive carnitine powder or granulate has a higher purity. Preferably the content of the accompanying substances in the inventive carnitine powder or granulate is less then 10%, more preferred less than 7%, even more preferred less than 5% and most preferred less than 2-3%. The content of carnitine in the inventive dry powder or granulate is at least about 8-10%, preferably more than about 30%, more preferred more than about 40% and most preferred more than about 50%, for example more than 60%, 70% or 80%. If an additional compound such an amino acid or a chromium compound was added during the preparation of the dry carnitine powder or granulate the powder/granulate contains corresponding amounts of that additional compound.

The inventive powder or granulate are dry in that they have a low water content. "Dry" means in particular a water content of less than 22%. In particular it is preferred that the water content of the L-carnitine powder is less than 12%, less than 8% or less than 6%. Most preferably, the water content of the powdery L-carnitine product according to the invention is less than 4% or even less than 2%.

The dried particulate carnitine powder according to the invention has an excellent flowability, good stability and storability. In comparison to a dried carnitine compound e.g. dry L-carnitine, it shows a considerably reduced hygroscopicity. Thus, the carnitine powder or granulate according to the invention may be maintained as such, i.e. as a dry powder/granulate, over long periods in a container without adsorbing water. The nature of the container is not critical. For example, it may be a glass jar or plastics box. It merely defines a storage environment within which there is no need to remove moisture or otherwise to control the conditions. During storage or in formulation, the inventive powdery or granular carnitine product may be mixed with any suitable bulking agents, other active ingredients, nutrients and the like and may be processed by any technique desired to give a finished product having the properties intended for the ultimate food, feed or therapeutic use. Such techniques are known to those skilled in the art.

In a particular preferred embodiment of the invention the dry carnitine powder or granulate is a dry L-carnitine powder or granulate. According to the invention the dry L-carnitine powder or granulate contains L-carnitine in an amount of at least about 8-10%, preferably more than about 30%, more preferred more than about 40% and most preferred more than about 50%, for example more than 60%, 70% or 80% relative to the total dry matter.

In another preferred embodiment the dry carnitine powder or granulate comprises as the carnitine compound a salt of carnitine with L-tartaric acid. Particularly preferred the dry carnitine powder or granulate comprises carnitine tartrate which is disclosed in U.S. Pat. No. 5,073,376, the entire disclosure of which is incorporated into the present text by reference. According to the invention the dry carnitine-tartrate powder or granulate contains the carnitin tartrate salt, in particular L-carnitine tartrate in an amount of at least about 8-10%, preferably more than about 30%, more preferred more than about 40% and most preferred more than about 50%, for example more than 60%, 70% or 80% relative to the total dry matter.

In a further preferred embodiment the dry carnitine powder or granulate comprises as the carnitine compound a salt of carnitine, in particular L-carnitine, with citric acid, (−)-hydroxycitric acid or ascorbic acid. The salt of carnitine, in particular L-carnitine, with citric acid, (−)-hydroxycitric acid or ascorbic acid can further comprise at least one alkaline earth metal cation wherein the metal cation is preferably selected from the group of magnesium and calcium. Such salts are disclosed in EP 1 326 502 B1 the entire disclosure of which is incorporated by reference into the present text.

In a particularly preferred embodiment the dry carnitine powder or granulate comprises L-carnitine-magnesium citrate. L-carnitine-magnesium citrate is disclosed in U.S. Pat. No. 5,071,874, the entire disclosure of which is incorporated into the present text by reference. According to the invention the dry L-carnitine-magnesium-citrate powder or granulate contains L-carnitine-magnesium citrate in an amount of least about 8-10%, preferably more than about 30%, more preferred more than about 40% and most preferred more than about 50%, for example more than 60%, 70% or 80% relative to the dry matter. The inventive L-carnitine-magnesium-citrate powder or granulate has in comparison to L-carnitine magnesium citrate salt a drastically reduced hygroscopicity.

In another particularly preferred embodiment the dry carnitine powder or granulate comprises carnitine-hydroxycitrate, preferably L-carnitine-hydroxycitrate. The carnitine-hydroxycitrate powder or granulate contains carnitine hydroxycitrate in an amount of at least about 8-10%, preferably more than about 30%, more preferred more than about 40% and most preferred more than about 50%, for example more than 60%, 70% or 80% relative to the dry matter.

In a further particularly preferred embodiment the dry carnitine powder or granulate comprises carnitine-magnesium hydroxycitrate disclosed in EP 1 326 502 B1 wherein magnesium, the carnitine compound and the hydroxycitrate are preferably present in a molar ratio of 1:1:1. The carnitine-magnesium-hydroxycitrate powder or granulate comprises carnitine-magnesium-hydroxycitrate in an amount of at least about 8-10%, preferably more than about 30%, more preferred more than about 40% and most preferred more than about 50%, for example more than 60%, 70% or 80% relative to the dry matter.

The dry carnitine powder or granulate obtained by any one of the inventive processes can be used either directly as foodstuff, feedstuff, cosmetic preparation and pharmaceutical composition, respectively, or for the preparation thereof.

Therefore, another aspect of the present invention relates to finished products containing at least one of the inventive dry carnitine powders or granulates, in particular solid finished products containing at least one of the inventive carnitine powders or granulates.

Such finished products can be obtained for example by mixing the inventive dry substantially pure and/or technical carnitine powder or granulate with one or more additional substances such as amino acids, e.g. lysine or a chromium compound. Alternatively, such finished products can be produced by admixing one or more of such additional substances to the carrier material which is added to the starting material. In a particular preferred embodiment the finished product is a foodstuff, feedstuff, pharmaceutical composition or cosmetic composition.

In a particularly preferred embodiment the finished product is a feed product comprising a L-carnitine powder according to the invention.

EXAMPLES

Material Used

Pre-Purified Starting Material Containing L-carnitine
L-carnitine ultrafiltration permeate 1 (L-carnitine=8.02% w/w, dry matter 9.87% w/w, salts+impurities 1.85% w/w, pH=6.5)
L-carnitine ultrafiltration permeate 2 (L-carnitine=7.90% w/w, dry matter 9.35% w/w, salts+impurities 1.45% w/w, pH=7.0)
Carrier Material
Wheat pollard batch No. S-224/04, CaCO$_3$ milled (S-219/04)
Sipernat 50, Sipernat 2200, Sipernat 22, Silcasil MG, TIX-O-SIL 68, Diamol DI 100 g
Equipment:
kitchen blender ETA 0010
laboratory spray drier with wheal atomiser (Anhydro),
laboratory whirl drier for drying of paste, set for Funnel test.
Methods:
a) Preparation of Mixtures
A calculated amount of a L-carnitine ultrafiltration permeate or powder was mixed with an corresponding amount of carrier (and chromium picolinate) either in laboratory beaker or in kitchen blender.
b) Drying
L-carnitine ultrafiltration permeate or suspensions or creams were stored at 4° C. and were dried either on laboratory spray drier at temperature inlet/outlet=250/115-120° C., or on laboratory whirl drier at temperature inlet/outlet=250/115-115° C.
c) Other Methods
The concentration of L-carnitine, 4-butyrobetaine, crotonobetaine and norcarnitine was determined by HPLC. The dry matter content was determined by drying in an oven at 105° C. till constant weight. The content of water was determined by the classical Carl-Fisher titration. The fluidity of the final products was measured by funnel test for determination of fluidity (see Technical Bulletin Pigments No. 3 of Degussa).

Example 1

Mixing of Spray-Dried L-carnitine Permeate with Carriers

In this experiment a L-carnitine permeate was spray-dried on a spray-drier and then mixed with appropriate carriers. The permeate was dried on a Niro atomizer (capacity 10 l H$_2$O/h) at an inlet temperatures of 230° C. (outlet temperature=115° C.). Thereby a dried but highly hygroscopic powder (content of L-carnitine about 86.2%) was obtained that contained lumps. The powder was quickly sieved to remove lumps and subsequently mixed in a kitchen blender with different amounts of diverse carrier materials which had been optionally mixed before with chromium picolinate. Table 1 shows the composition of the thus obtained dry L-carnitine powders.

TABLE 1

| L-carnitine powder | Dried permeate (g) | Wheat pollard (g) | CaCo$_3$ (g) | Diamol (g) | Chromium picolinate (g) |
|---|---|---|---|---|---|
| 1 | 40.5 | 206.2 | 103.1 | 0 | 0 |
| 2 | 206 | 0 | 0 | 146.5 | 0 |
| 3 | 206 | 0 | 0 | 140.9 | 5.6 |

Due to the hygroscopic nature of the dried permeate it thus was difficult to prevent mounting of the dried material and formation of lumps in the device used for drying. Therefore lumps had to been removed by sieving. The danger of re-wetting of the sieved material could be prevented by using an atmosphere of nitrogen.

Example 2

Drying of Mixtures of L-carnitine Permeates and Carriers

In this experiment L-carnitine permeate was mixed with carriers and subsequently dried on suitable drying devices. If the mixture was liquid a spray-dryer was used. If the mixture had the form of a paste a whirl-dryer was used. Table 2 shows the composition of the thus obtained dry L-carnitine powders.

TABLE 2

| carnitine powder No. | Wheat pollard (g) | Calcite (g) | Diamol (g) | Chromium picolinate (g) | Permeate (g) | Consistency of mixture | Dryer used |
|---|---|---|---|---|---|---|---|
| 4 | 206.2 | 103.1 | 0 | 0 | 437.5 | loupes | whirl |
| 5 | 103.1 | 206.2 | 0 | 0 | 437.5 | Rare paste | |
| 6 | 0 | 309.3 | 0 | 0 | 437.5 | slurry | Spray |
| 7 | 0 | 0 | 146.5 | 0 | 2188 | Rare slurry | spray |
| 8 | 0 | 0 | 140.9 | 5.6 | 2188 | Rare slurry | spray |

The overall characteristics such as appearance, flowability, stability and workability of the L-carnitine powders 4-8 was better than that of L-carnitine powders 1-3 prepared in example 1. The physical behaviour of L-carnitine powder no. 4 was excellent. The product consisted of coarser particles and In comparison to powders no. 6, 7 and 8 which consisted of fine particles and had a tendency to dampness, powder no. 4 consisted of somewhat coarser particles and had no tendency to dampness.

The composition of the L-carnitine powders 4-8 is shown in Table 3.

| L-carnitine powder No. | Content of L-carnitine (%) | Content of water (%) |
|---|---|---|
| 4 | 9.05 | 9.13 |
| 6 | 10.76 | 1.01 |
| 7 | 48.2 | 2.19 |
| 8 | 50.21 | 2.78 |

Example 3

Drying of mixtures of L-Carnitine Permeates and Microgranulated Carriers on a Production Scale In this production experiment L-carnitine permeate was mixed with carriers and subsequently dried on suitable drying devices whereby a fluid mixture obtained. For drying la spray-dryer with fluid bed was used. Table 4 shows the composition of the thus obtained dry L-carnitine microgranulates.

TABLE 4

| Carnitine powder No. | Wheat pollard (g) | Calcite (g) | TilX-O-SIL 68 (kg) | Chromium picolinate (kg) | Permeate (g) | Consistency of mixture | Dryer used |
|---|---|---|---|---|---|---|---|
| 9 | 0 | 0 | 1430 | 0 | 21880 | rare slurry | spray with fluid bed |
| 10 | | | 1440 | 56 | 22000 | rare slurry | spray with fluid bed |

The overall characteristics such as appearance, flowability, stability and workability of the L-carnitine powders 9 and 10 were better than that of powders 3, 6, 7 and 8. Both products consist of coarser regular particles (70% of products size 106-212 μm with negligible amount of dust (size below 53 μm less then 0.1%).

The composition of the L-carnitine powders 9-10 is shown in Table 5.

| L-carnitine powder No. | Content of L-carnitine (%) | Content of water (%) |
|---|---|---|
| 9 | 52.3 | 2.38 |
| 10 | 51.8 | 2.22 |

The invention claimed is:

1. A process for preparing a dry carnitine powder or granulate from a liquid starting material containing carnitine and accompanying substances, said process comprising the steps of:
   a) obtaining a liquid starting material comprising an unpurified fermentation broth formed by a biocatalytic process for the production of carnitine in a liquid medium;
   b) subjecting the liquid starting material of step a) to one purification or one separation step to obtain a pre-purified liquid starting material containing carnitine and accompanying substances, wherein the pre-purified liquid starting material contains an amount of total dry matter, wherein the accompanying substances in the total dry matter is in the range of 10% to less than 50% of the total dry matter;
   c) mixing the pre-purified starting material of step b) with a carrier;
   d) subjecting the mixture obtained in step c) to a drying process, wherein the drying process occurs after only one purification or one separation step being performed on the liquid starting material; and
   e) recovering a stable dry carnitine powder or granulate, wherein the content of the accompanying substance of the pre-purified starting material in the recovered carnitine powder or granulate is less than 10% and wherein the carnitine is 1-carnitine, an alkanoyl-1-carnitine, a salt thereof or a mixture thereof.

2. A process for preparing a dry carnitine powder or granulate from a liquid starting material containing carnitine and accompanying substances, said process comprising the steps of:

a) obtaining a liquid starting material comprising an unpurified fermentation broth formed by a biocatalytic process for the production of carnitine in a liquid medium;

b) subjecting the liquid starting material of step a) to one purification or one separation step to obtain a pre-purified liquid starting material containing carnitine and accompanying substances, wherein the pre-purified liquid starting material contains an amount of total dry matter, wherein the accompanying substances in the total dry matter is in the range of 10% to less than 50% of the total dry matter;

c) subjecting the pre-purified liquid starting material of step b) to a drying process to obtain a dried product, wherein the drying process occurs after only one purification or one separation step being performed on the liquid starting material;

d) mixing the dried product of step c) with a carrier; and e) recovering a stable dry carnitine powder or granulate, wherein the content of the accompanying substances of the pre-purified starting material in the recovered carnitine powder or granulate is less than 10%, and wherein the carnitine is 1-carnitine, an alkanoyl-1-carnitine, a salt thereof or a mixture thereof.

3. The process according to claim 2 wherein the dried product is sieved to remove lumps and then mixed with the carrier.

4. The process according to claim 2 wherein the pre-purified starting material has the form of a solution, suspension or paste.

5. The process according to claim 2 wherein the drying process is a spray-drying.

6. The process according to claim 2 wherein the drying is conducted in a whirl drier.

7. The process according to claim 2 wherein the carrier is selected from the group consisting of wheat pollard, precipitated silica, silica particles, floury or granulated 35 diatomaceous earth and calcium carbonate.

8. The process according to claim 7 wherein one or more additional compounds are added to the pre-purified starting material or to the carrier before drying or to the dry carnitine powder obtained after drying.

9. The process according to claim 8 wherein the additional ingredient is a chromium compound.

10. The process according to claim 8 wherein the additional ingredient is an amino acid.

11. The process according to claim 8 wherein the dry carnitine powder has a water content of less than 12%.

12. The process according to claim 11 wherein the dry carnitine powder is suitable for the production of a feed product.

13. The process according to claim 1 wherein the pre-purified starting material has the form of a solution, suspension or paste.

14. The process according to claim 1 wherein the drying process is a spray-drying.

15. The process according to claim 1 wherein the drying is conducted in a whirl drier.

16. The process according to claim 1 wherein the carrier is selected from the group consisting of wheat pollard, precipitated silica, silica particles, floury or granulated 35 diatomaceous earth and calcium carbonate.

17. The process according to claim 1 wherein one or more additional compounds are added to the pre-purified starting material or to the carrier before drying or to the dry carnitine powder obtained after drying.

18. The process according to claim 1 wherein the dry carnitine powder has a water content of less than 12 percent.

* * * * *